US006406879B2

(12) United States Patent
James et al.

(10) Patent No.: US 6,406,879 B2
(45) Date of Patent: *Jun. 18, 2002

(54) DEVICE AND METHOD FOR TESTING BIOCIDAL EFFICACY OF A LIQUID

(75) Inventors: Phillip Richard James, Leicester; Richard Mark Bancroft, Coalville, both of (GB)

(73) Assignee: Albert Browne Limited (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/052,303

(22) Filed: Mar. 31, 1998

(30) Foreign Application Priority Data

Apr. 4, 1997 (GB) .............................................. 9706902

(51) Int. Cl.⁷ ........................... A01N 25/00; C12M 1/34; C12M 3/00; C12N 1/00; C12Q 1/00
(52) U.S. Cl. ........................... 435/32; 424/405; 435/29; 435/30; 435/31; 435/243; 435/287.1; 435/287.4
(58) Field of Search .......................... 435/32, 243, 287, 435/405, 4, 31, 287.1, 287.4, 404, 29, 30; 424/405

(56) References Cited

U.S. PATENT DOCUMENTS 3,999,945 A * 12/1976 Kushner et al. .......... 23/253 R
5,407,269 A * 4/1995 Sherry et al. ............. 366/174.1
5,443,985 A * 8/1995 Lu et al. ................. 435/240.25

FOREIGN PATENT DOCUMENTS

| DE | 37 05 596 A | 9/1988 |
| EP | 0 555 605 A | 8/1993 |
| WO | WO 96 06184 A | 2/1996 |
| WO | WO 97 05274 A | 2/1997 |

* cited by examiner

Primary Examiner—David M. Naff
Assistant Examiner—Deborah K. Ware
(74) Attorney, Agent, or Firm—Nixon Peabody LLP

(57) ABSTRACT

A test device and a method for assessing the biocidal efficacy of a liquid are disclosed. The device includes: a vessel, an inlet in communication with said vessel, means for introducing a predetermined volume of a liquid into said vessel via said inlet in a first direction, a porous filter interposed between said inlet and said vessel, and a predetermined quantity of biologically active organisms positioned within a region defined by said vessel and said porous filter, said region being on a side of said porous filter which is opposite said inlet, wherein said means for introducing a predetermined volume of the liquid also operates to expel the liquid from said vessel via the same inlet through which it was originally introduced but in a second reverse direction and wherein said filter has a pore size effective to retain said organisms in said region to assess the biocidal activity of the liquid and prevent said organisms from being expelled with the liquid when said means for introducing a predetermined volume of the liquid is operated to expel the liquid.

15 Claims, 1 Drawing Sheet

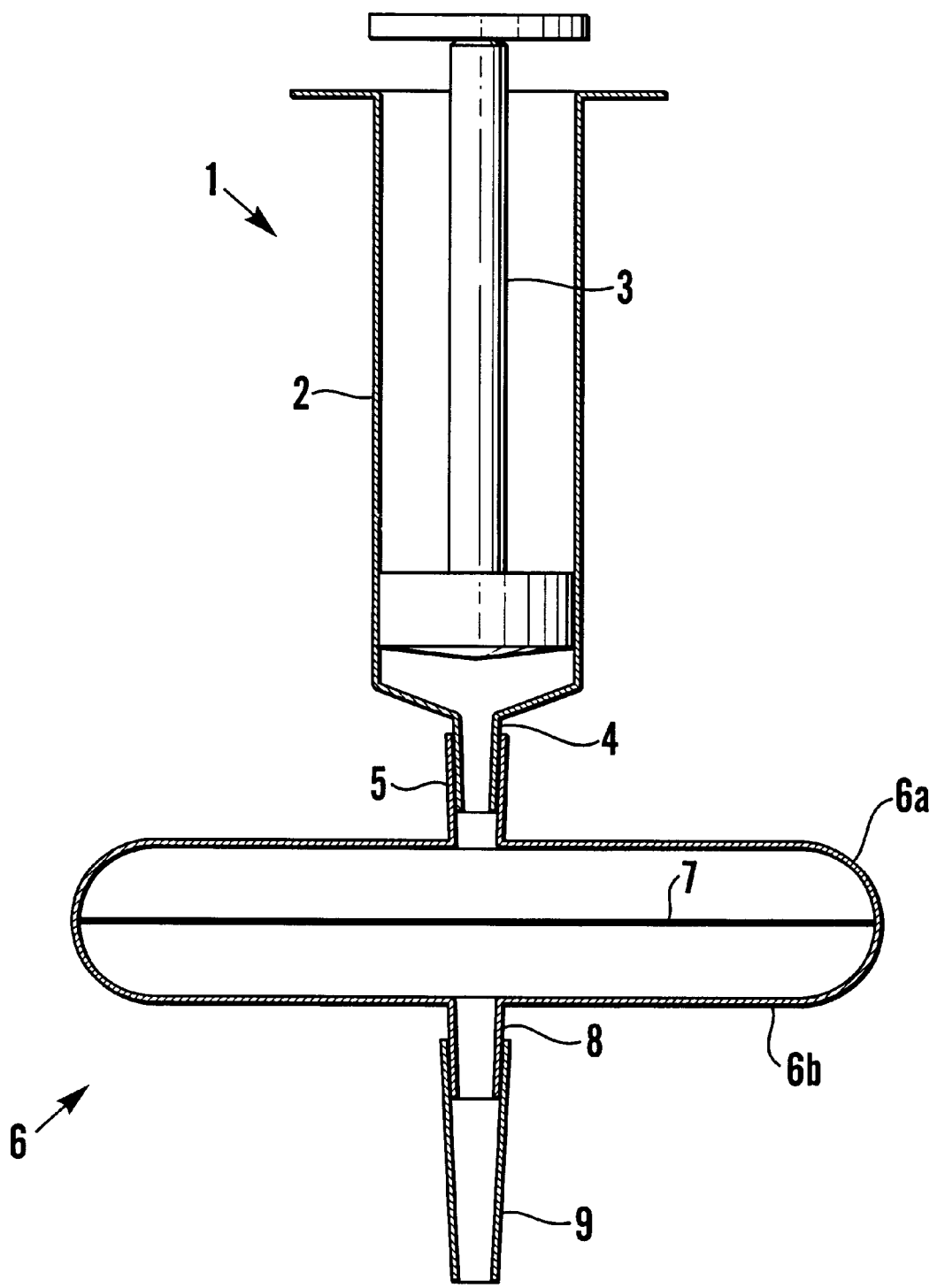

DEVICE AND METHOD FOR TESTING BIOCIDAL EFFICACY OF A LIQUID

FIELD OF THE INVENTION

This invention relates to a test device and method, in particular to a device and method for testing the biocidal efficacy of a liquid sterilant.

BACKGROUND OF THE INVENTION

The efficacy of sterilization processes is generally assessed by the use of biological indicators; these consist of a known number of micro-organisms, established as having a high resistance to the particular process, attached to or suspended on an inert carrier. For most sterilization processes, the use of bacterial spores inoculated onto a paper disc carrier is sufficient.

When dealing with liquid sterilants, however, there is a danger of release of the bacterial spores into the sterilization fluid medium. A conventional carrier is therefore inappropriate due to a likelihood of contamination of the sterilization fluid.

There has now been devised a test device and method which overcomes or substantially mitigates the problems associated with conventional methods of testing liquid sterilants.

SUMMARY OF THE INVENTION

According to the invention, a test device for assessing the biocidal efficacy of a liquid comprises a vessel, means for introducing a predetermined volume of the liquid into the vessel via an inlet, and a porous filter interposed between the inlet and the vessel, wherein the vessel contains a predetermined quantity of biologically active organisms and the filter has a pore size effective to retain said organisms.

According to another aspect of the invention, a method for assessing the biocidal efficacy of a liquid comprises a) providing a vessel in communication with an inlet and containing a known quantity of biologically active organisms, the inlet being separated from the vessel by a porous filter having a pore size effective to retain said organisms, b) introducing a predetermined volume of the liquid into the vessel via the inlet, c) removing the liquid from the vessel via the inlet or via an outlet with a similarly effective filter, d) introducing a culture medium for the biologically active organisms into the vessel, and e) ascertaining whether growth of biologically active organisms takes place in the culture medium.

The device and method of the invention are advantageous primarily in that they enable testing of the biocidal activity of a liquid without the risk of contamination of the liquid with organisms utilised in the test procedure.

BRIEF DESCRIPTION OF THE DRAWING

FIG. 1 shows the device for testing the efficacy of a liquid.

DETAILED DESCRIPTION OF THE INVENTION

In a preferred embodiment, the vessel takes the form of a syringe. The syringe plunger is used to draw up the predetermined volume of liquid and subsequently to expel the liquid and to draw up the culture medium.

The filter is preferably housed in a filter unit attached to the syringe. Both the syringe and the filter unit are preferably disposable. The syringe is preferably of the disposable polyethylene or polypropylene type, equipped with a luer lock hub, generally with a capacity not exceeding ten millilitres. The filter unit is preferably of the disposable sealed unit type, in which the housing may consist of polyethylene, polyvinyl chloride, polypropylene, polystyrene or similar polymers. The housing preferably possesses a luer lock inlet.

The filter unit preferably contains a filter membrane, most preferably in disc form. The membrane may consist of cellulose esters, polytetrafluoroethylene, polyvinylidene difluoride, nylon, polycarbonate or any other suitable polymer, or glass fibre material. In addition, the membrane may be pre-treated so as to create hydrophilic and hydrophobic regions.

Polytetrafluoroethylene is a currently preferred membrane material.

Most preferably, the predetermined quantity of biologically active organisms is deposited on the filter, on the side of the filter connected to the syringe. The organisms may be deposited on the membrane by a number of methods, including passing a suspension of organisms through the membrane, or depositing a suspension of organisms, in a volatile solvent, on the membrane and allowing the solvent to evaporate.

The method of the invention may comprise time delays between steps b) and c), and/or between steps d) and e). In addition, one or more washing steps, eg comprising introduction and removal of an appropriate rinsing agent, eg water, may take place between steps c) and d).

The step of ascertaining whether growth of biologically active organisms has taken place in the culture medium may comprise visual inspection, eg for the presence of turbidity.

The method and device of the invention may be utilised in connection with any form of biologically active organism which is conventionally killed using a liquid sterilant. One example is bacterial spores.

The invention will now be described in greater detail, by way of illustration only, with reference to the accompanying drawing which shows a schematic sectional view of a device according to the invention.

Referring to the drawing, a device for testing the efficacy of a sterilant liquid is generally designated 1 and comprises a disposable clear plastics syringe 2 with a plunger 3. The syringe 2 has a nozzle 4 which is fixed in a corresponding luer lock neck 5 of a filter unit 6.

The filter unit 6 is also disposable and of clear plastics material, and takes the form of a hollow disc. The unit 6 comprises upper and lower (as viewed in the drawing) halves 6a, 6b which are joined at their adjoining peripheries and which sandwich a disc 7 of porous membrane material between them. The lower half 6b has a central open spigot 8 on which a spout 9 is fitted.

The upper (as viewed in the drawing) surface of the membrane disc 7 is inoculated with a known quantity of bacterial spores.

In use, a defined quantity of test sterilant is drawn into the device 1 (ie through the inoculated membrane 7 connected by luer lock to the syringe 2) by raising the plunger 3, and is allowed to remain in the device for the required sterilization time. At the end of this period, the sterilant is ejected from the device 1 by depressing the plunger 3, and discarded. To remove residual sterilant, an equal volume of de-ionised or purified water is drawn into the device 1 and ejected, and this step is repeated. An equal amount of a specified culture medium, known to support growth of the bacterial spores, is then drawn into the device 1, and this is incubated under the specified conditions. If necessary or desired, a cap or the like (not shown) may be fitted over the end of the spout 9 after introduction of the culture medium. At the end of this stage, the medium in the device **1